United States Patent [19]

Daikuzono

[11] Patent Number: 5,380,318

[45] Date of Patent: Jan. 10, 1995

[54] CONTACT OR INSERTION LASER PROBE HAVING WIDE ANGLE RADIATION

[75] Inventor: Norio Daikuzono, Tokyo, Japan

[73] Assignee: Surgical Laser Technologies, Inc., Oaks, Pa.

[21] Appl. No.: 212,653

[22] Filed: Mar. 11, 1994
(Under 37 CFR 1.47)

Related U.S. Application Data

[63] Continuation of Ser. No. 824,823, Jan. 22, 1992, abandoned, which is a continuation of Ser. No. 273,304, Nov. 18, 1988, abandoned, which is a continuation-in-part of Ser. No. 124,448, Nov. 24, 1987, abandoned, which is a continuation of Ser. No. 862,114, May 12, 1986, abandoned.

[51] Int. Cl.$^6$ ............................................. A61B 17/32
[52] U.S. Cl. ........................................................ 606/16
[58] Field of Search ................................... 606/13–16, 606/17

[56] References Cited

U.S. PATENT DOCUMENTS

| | | | |
|---|---|---|---|
| 247,231 | 9/1881 | Wheeler | 128/23 |
| 1,794,557 | 3/1931 | Symonds . | |
| 2,056,990 | 10/1936 | Symonds | 128/398 |
| 2,247,258 | 6/1941 | Shepard | 128/397 |
| 3,304,403 | 2/1967 | Harper | 219/121 |
| 3,467,098 | 9/1969 | Ayres | 128/303.1 |
| 3,528,424 | 9/1970 | Ayres | 128/303.1 |
| 3,622,743 | 11/1971 | Muncheryan | 128/303.1 |
| 3,638,644 | 2/1972 | Reick | 128/16 |
| 3,794,091 | 2/1974 | Ersek et al. | 128/23 |
| 3,821,510 | 6/1974 | Muncheryan | 128/395 |
| 3,834,391 | 9/1974 | Block | 128/303.1 |
| 3,865,113 | 2/1975 | Sharon et al. | 128/303.1 |
| 3,890,960 | 6/1975 | Worsch | 128/16 |
| 4,126,136 | 11/1978 | Auth et al. | 606/17 |
| 4,266,549 | 5/1981 | Kimura | 128/303.1 |
| 4,422,719 | 6/1981 | Orcutt | 350/96.3 |
| 4,470,414 | 9/1984 | Imagawa et al. | 128/303.1 |
| 4,592,353 | 6/1986 | Daikuzono | 128/303.1 |
| 4,693,244 | 9/1987 | Daikuzono | 606/16 |
| 4,736,743 | 4/1988 | Daikuzono | 606/16 |

FOREIGN PATENT DOCUMENTS

| | | |
|---|---|---|
| 161606 | 11/1985 | European Pat. Off. . |
| 60-45529 | 10/1985 | Japan . |
| 60-190310 | 12/1985 | Japan . |
| 61-135649 | 6/1986 | Japan . |
| 61-181456 | 8/1986 | Japan . |
| 61-209648 | 9/1986 | Japan . |
| 63-111857 | 5/1988 | Japan . |
| 63-180817 | 11/1988 | Japan . |
| 2154761 | 9/1985 | United Kingdom . |
| 1118371 | 10/1984 | U.S.S.R. ............................ 128/395 |
| 8505262 | 12/1985 | WIPO . |

OTHER PUBLICATIONS

Doty et al., "The Laser Photocoagulation Dielectric Waveguide Scalpel" Jan. 1981 IEEE . . . Biomed. Engin.

Chang et al. "Radiation characteristics of a tapered cyl. optical fiber" Sep. 1978 J. Opt. Soc. Am.

Daikuzono et al. "Artificial Sapphire . . . ND:YAG Laser " Jul.-Aug. 1985 Med. Instr.

Fujii, H. et al. "Light Scattering properties of a rough-ended optical fibre", *Optics and Laser Technology*, vol. 16, No. 6, Feb. 1984, 40–44.

Fujii et al. "Interstitial Irradiation with Roughened Optical Fiber End," *The Journal for Japan Society for Laser Medicine*, vol. 3, No. 1, Nov. 19, 1982, 183–188.

*Primary Examiner*—Max Hindenburg
*Attorney, Agent, or Firm*—Seidel, Gonda, Lavorgna & Monaco

[57] ABSTRACT

A laser medical probe adapted for direct contact with, or insertion into, tissue undergoing laser treatment. The probe includes a laser energy transmissive surface for emitting radiation from the probe. The probe surface includes a layer of laser transmissive particles for diffusing laser energy passing therethrough and an affixing material for affixing the particles to the probe surface. Laser energy emitted from the surface may be coupled into the particles and irregularly refracted and reflected thereby causing a wide laser energy radiation profile. The affixing material and the particles form a tissue contact surface for directly contacting the tissue undergoing treatment. A substantial number of the particles partially extend from the affixing material. The resultant tissue contact surface is rough. The affixing material may be a ceramic bonding agent.

57 Claims, 5 Drawing Sheets

CONTACT OR INSERTION LASER PROBE HAVING WIDE ANGLE RADIATION

This is a continuation of co-pending application Ser. No. 07/824,823 filed on Jan. 22, 1992, now abandoned which is a continuation of application Ser. No. 07/273,304 filed on Nov. 18, 1988, abandoned, which is a continuation-in-part of application Ser. No. 07/124,448 filed Nov. 24, 1987, now abandoned, which is a continuation-in-part of application Ser. No. 06/862,14 filed May 12, 1986, now abandoned.

This invention relates to a medical probe used for effecting hyperthermia, coagulation or hemostasis with respect to tissues of human or animal organisms by laser irradiation thereof.

There have been recent advances in the field of laser surgery particularly in connection with Nd:YAG lasers and the use of contact laser probes wherein, contrary to established convention, the probe may be brought into direct contact with the tissue. The numerous advantages of contact laser surgery are described in U.S. Pat. No. 4,592,353, owned by the present assignee.

Whether of a contact or non-contact variety, it is known that penetration of laser energy into tissue is limited and, therefore, laser treatment of sub-surface tissue requires removal or cutting of the overlying surface tissue. This characteristic of laser surgery does not represent a problem during many procedures, for example incision, where it is the very purpose of the procedure to cut through the surface layers of tissue.

On the other hand, there are other procedures in which it is desirable to laser irradiate tissue lying below the surface without irreparably damaging the tissue thereabove. One such procedure, known as PRT (photoradiation therapy), is reported to selectively break cancerous tissue when the tissue has been pre-treated with a photosensitizer. (See Doughterty, T. J., et al.: Photoradiation Therapy for the Treatment of Malignant Tumors. Cancer Res., 38: 2628-2635, 1978). PRT involves the intravenous injection of photosensitizer, generally hematoporphyrin derivatives (HpD), approximately 48 to 72 hours before tissue irradiation by an argon dye laser. It has been observed that cancerous tissues are destroyed while the normal tissues remain virtually unaffected.

It will be appreciated that PRT treatment requires the irradiation of the entire cancerous area, such area generally lying well below the tissue surface. It is therefore preferable, if not necessary, that the laser probe be inserted into the tissue so that the laser beam may sufficiently react with the photosensitizer. Further, it is necessary that the tip exhibit a broad radiation pattern to insure the widest possible illumination of presensitized cancerous tissue.

Known laser probes, however, emit laser energy only from the tip region of the probe and, then, only in a relatively narrow beam directed substantially outwardly and downwardly (i.e. axially) form the probe tip. When such a tip is inserted into the cancerous tissue, two problems are seen to occur. First, the relatively narrow illumination pattern, for example 8 to 14 degrees, results in a correspondingly limited tissue treatment region. As it is necessary to expose tissue for about 15 to 35 minutes, it takes considerable time to irradiate any but the smallest areas requiring treatment. The second problem encountered with conventional probes is the charring of tissue immediately adjacent the probe tip due to the high power density of the concentrated laser beam in that region. Charring prevents the laser beam from penetrating the charred portion of the tissue, in turn, remarkably lowering the overall penetration of the laser beam.

In addition to PRT, a probe which is capable of widely diffusing the laser beam may advantageously be utilized for the treatment of gastric cancer, ulcer, gastric or intestinal hemorrhage, or local hyperthermia. For local hyperthermia a Nd:YAG laser may also be employed.

The preferred arrangement of the present invention is a conically shaped probe of quartz, sapphire, or diamond. While the design of such a probe can be varied to either facilitate or inhibit radiation from the sides of the conical probe tip, the resulting radiation pattern will, absent the teachings of the present invention, remain substantially outward along the axis of the probe. The area of illumination remains limited.

The present invention, therefore, relates to a laser probe having a substantially wider radiation pattern, in fact, a pattern in which both radial sideways as well as rearward backscattering may be achieved in addition to nominal forward radiation. The present probe tip achieves not only broader tissue illumination, but importantly, it does so at substantially more uniform laser energy densities thereby greatly minimizing the likelihood of tissue charring. In particular, in one of the embodiments of the invention, the present probe tip is characterized by an uneven or roughened surface having recesses therein ranging in depth preferably from about 1 to 100 $\mu$m. As a result, some of the laser energy which reaches this surface is reflected while the remainder is radiated generally to the tissue adjacent thereto.

Thus, the laser beam impinging on this surface from within the tip is, in part, refracted directly to the tissue and, in part, further reflected irregularly within the concaved portions of the uneven roughened surface. This scattering of the beam occurs over the entire roughened surface of the probe so that the emitted laser energy impinges the tissue substantially from all directions thereby broadening the radiation area and increasing penetration into the tissue by lowering local charring of the tissue.

In a further embodiment of the probe of the present invention, there is provided a tapered, preferably conical, laser tip member having a diffusing layer applied to the smooth outer surface thereof. The diffusing layer comprises a plurality of laser transmissive particles, which may or may not be of the same material from which the laser probe body is made, bound by a ceramic material to the outer surface of the probe tip. This probe is similarly adapted to transmit laser energy radially and axially to the tissue.

The diffusing layer (also referred to herein as the particulate layer) adheres to the probe tip and functions to diffuse laser energy generally radially, as well as axially, to the area adjacent the probe tip. Preferably, the diffusing, particulate layer comprises natural diamond particles, although sapphire or quartz, or a synthetic or polymeric material, such as synthetic diamond crystals may be employed. The laser transmissive particles should be in the range of about 0.1 to about 50 $\mu$m in size. As described in more detail below., the laser diffusing layer is made by binding diamond particles (e.g., diamond dust) or other laser transmissive particles to a probe tip, so that said particles are in energy-transmitting communication with the probe tip, a ceramic material binding the particulate to the probe tip.

Due to the generally high refractive index of the diffusing particles and the lowered ratio of refractive indices defined at the boundary between the probe and its surroundings, but caused by the presence of the particles, a significant portion of the laser energy which internally impinges this outer tip boundary will be refracted or coupled into the diffusing particles from where such energy will be directly radiated to the adjacent tissue, or internally reflected one or more times within the diffusing particulate material until finally radiating therefrom or reflected back into the probe tip and emitted elsewhere. Whether laser energy is refracted or reflected will depend on the angle of incidence, the ratio of the refractive indices of the probe tip and diffusing particles, and the refractive index of the particles of the diffusing layer.

Although it is preferred that the particulate layer contain particles of a laser transmissive material which have a higher refractive index than that of the probe tip—thus the use of diamond dust—a particulate layer comprising the same material or a material having somewhat lower refractive index than that of the probe tip, is also contemplated. It is believed that lowering the ratio of the refractive index of the probe relative to the refractive index of the particles of the diffusing layer causes the desirably enlarged area of diffused irradiation which is directed radially and axially with respect to the direction of wave propagation in a conventional probe tip. Moreover, irregularly shaped particles of relatively high refractive index in the diffusing layer enhances this diffusion.

In yet another embodiment of the invention, there is provided a medical laser probe adapted to transmit laser energy propagated through an optical waveguide to provide energy for treatment of tissue. In this embodiment, the core of the probe is hollow and the inner surface of the probe defines the laser diffusing member, said laser diffusing member comprising a frosted or roughened face, or a particulate diffusing layer which comprises irregularly shape refractive particles, as disclosed above.

This form of the probe is characterized in that the frosted or roughened surface or the diffusing particulate layer is formed on the inner face of the laser diffusing member. The laser beam is partially transmitted through the diffusing member of the inner surface and partially reflected irregularly to reach another portion of the probe where the laser beam is transmitted or again reflected irregularly. As a result, laser energy is radiated from a wide outer surface of the probe at substantially uniform power density. In this case, the laser radiating area may be wide, for example, on a round surface of large diameter so that it may be used in a mode contacting with the surface of the tissue for effecting the coagulation of the tissue.

It is therefore an object of the present invention to provide a probe which is capable of irradiating a wide surface area in a diffused irradiation mode.

It is another object of the present invention to provide a probe which is capable of emitting laser beam from all over the irradiating surface area with substantially uniform power density.

Further objects will be apparent from the following description.

DESCRIPTION OF THE PREFERRED EMBODIMENT

Figure 1:
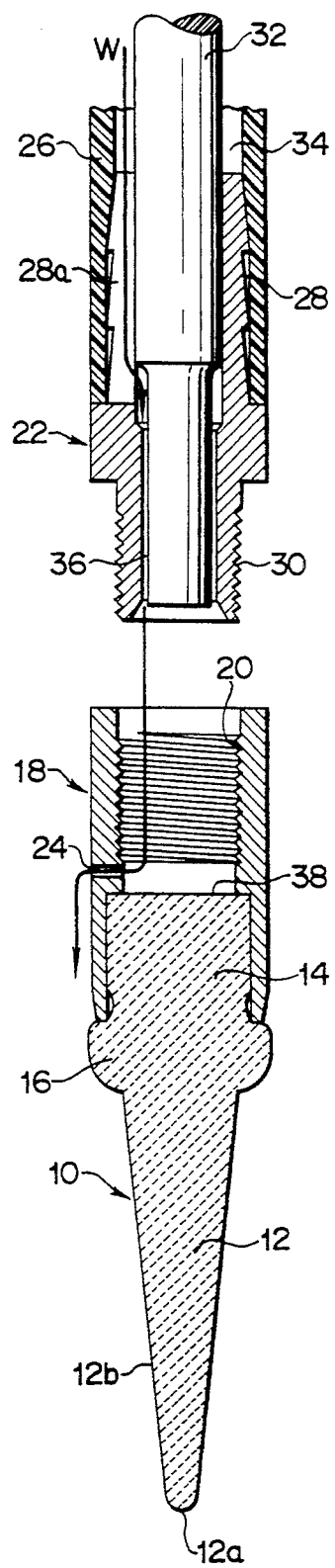
FIG. 1 is an elevation view, part in section, of the probe of the present invention and a holding member therefor.

FIG. 1 is a longitudinal sectional view of a probe 10 according to the present invention which is mounted at the terminal or output end portion of a laser optical waveguide fiber 32.

Probe 10 is made of a laser transmissive material such as a natural or artificial ceramic material, for example, sapphire, quartz, or diamond. Polymeric materials may also be employed. In the embodiment as illustrated, the probe 10 comprises a conically tapered laser diffusing portion 12 having, at the tip end thereof, a semispherical portion 12a and a main body portion 14. The laser diffusing portion 12 and the main body portion 14 are formed integrally with each other and a flange 16 is formed between the laser diffusing portion 12 and the main body portion 14. The probe 10 is fitted in a cylindrical female connector 18 and fixed integrally thereto by caulking the mating surfaces thereof or using a ceramic type adhesive between the mating surfaces. The female connector 18 has, on the internal surface thereof, a thread 20 which is adapted to mate with complementary threads 30 of a male connector 22. The female connector 18 has two holes 24 through the cylindrical connector wall which facilitate the passage of cooling water W or other fluids therethrough. The two holes are circumferentially disposed at angular spaces of 180° although only one of them is shown in FIG. 1.

On the other hand, the male connector 22 is pressedly fitted into a flexible tube of jacket 26 fabricated of, for example, Teflon (trademark). For this press fitting, the male connector 22 has stepped portions 28 at the base portion of the male connector 22 by which the male connector 22 is firmly held within jacket 26 so as to prevent the former from being disengaged from the latter. As noted, male connector 22 is externally threaded at 30 to mate with the internal thread 20 of the female connector 18.

An optical fiber 32 for transmitting the laser beam is inserted in the male connector 22. The optical fiber 32 is disposed concentrically within the jacket 26, leaving a gap 34 therebetween for passage of cooling water or other fluids. Although the fiber 32 is closely fitted in the male connector 22 adjacent the stepped portion of the male connector, the stepped portion 28 has for example two slits 28a formed circumferentially at angular spaces of 180° for letting the cooling water W pass therethrough. A passage 36 for the cooling water W is further provided between the inner face of the tip end portion of the male connector 22 and the optical fiber 32. The assembled tip may then be inserted into an endoscope or otherwise positioned as required for the laser surgical procedure to be performed.

The fiber 32 is optically connected to a laser generating unit (not shown). According to necessity, cooling water W is fed through the gap 34; slit 28a; passage 36 then, in turn, discharged through the opening 24 to cool the tissue to be treated.

The laser beam from the laser generating unit is guided through the optical fiber 32 and coupled from the end thereof into the base 38 of probe 10. The laser beam is thereafter emitted, as discussed in more detail below, from the diffusing portion 12 of the tip to the tissue M to be treated.

Figure 2:
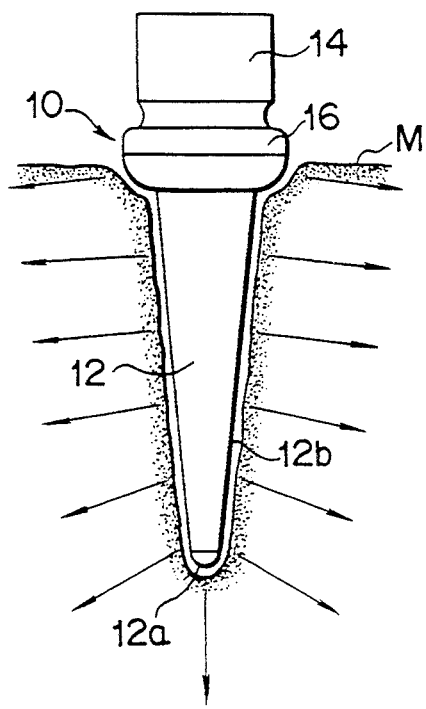
FIG. 2 is an elevation view showing the probe of FIG. 1 inserted into the tissue and irradiating the tissue adjacent thereto.

FIG. 2 illustrates the dispersion and diffusion of laser beam when the probe of the present invention is employed. As will be described later, the outer surface of the laser diffusing portion 12 of the probe 10 is frosted or roughened, thereby widely dispersing the laser energy as illustrated in FIG. 2.

Figure 6:
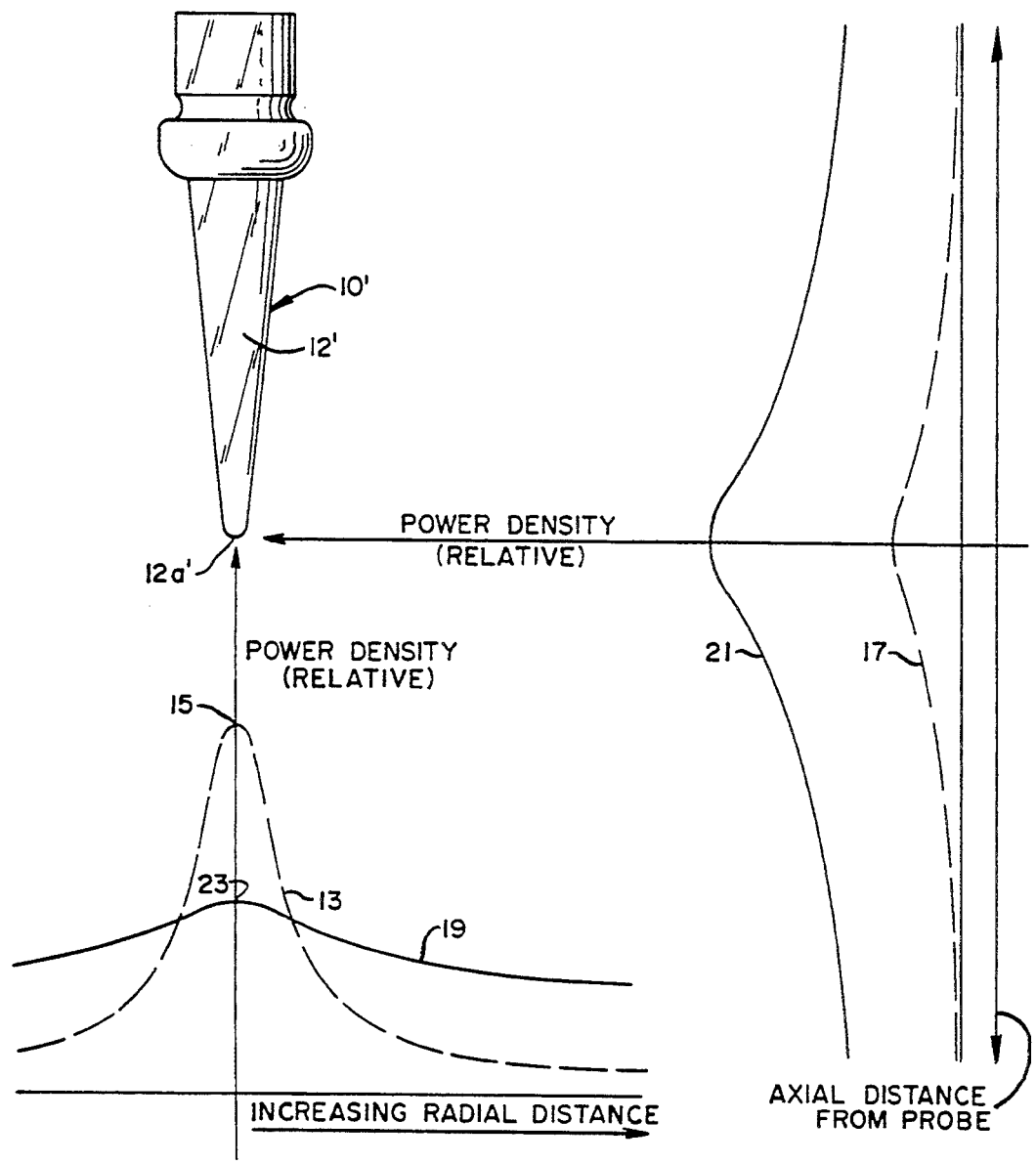
FIG. 6 is a distribution diagram comparing the radiated power densities of the present probe against non-diffusing probes.

FIG. 6 best illustrates the comparative radiation energy densities between a prior art probe tip and the probe tip of the present invention. Probe 10' represents both the present and prior art laser tips when viewing the solid 21, 23 and dotted 13, 17 line curves, respectively. Curve 13 represents the laser energy or power density distribution in a plane spaced below the probe tip and perpendicular to the longitudinal axis thereof. More specifically, the power density is shown to be greatest at 15, a point along the extended longitudinal axis of the probe tip, and to diminish rapidly as the distance from this axis is increased. Curve 17 very roughly approximates the laser power density distribution in a cylindrical surface surrounding the probe and having a common axis thereto. This curve essentially depicts the radial component of laser radiation which, as can be seen, is extremely low in a conventional tip due to the fact that substantially all of the laser energy is radiated longitudinally downwardly from tip 12a'. Curve 17, therefore, is merely intended to depict this low level of radial radiation rather than to accurately illustrate the actual power distribution.

Curves 19 and 21 represent the laser power density distributions for the probe of the present invention corresponding, respectively, to prior art probe curves 13 and 17. As can be seen from curve 19, the peak power density 23 along the probe center axis is substantially lower than that of the prior art tip and, importantly, the power density drops less rapidly as a function of distance from this axis. This produces a broad area of relatively uniform laser illumination while simultaneously avoiding the excessive on-axis power densities which result in tissue charring. Curve 21 reveals that substantial laser energy is emitted radially from the probe of the present invention and, further, that such radiation is not limited to the tip region 12a', but occurs along the entire length of the conical diffusing portion 12' of the probe. However, as discussed in more detail below, the laser power distribution depicted by curve 21 is, in reality, achieved by the random refraction and scattering of laser energy within the probe tip and, therefore, this radiation, while illuminating tissue along the side of the tip, is not necessarily emitted radially therefrom.

Figure 3:
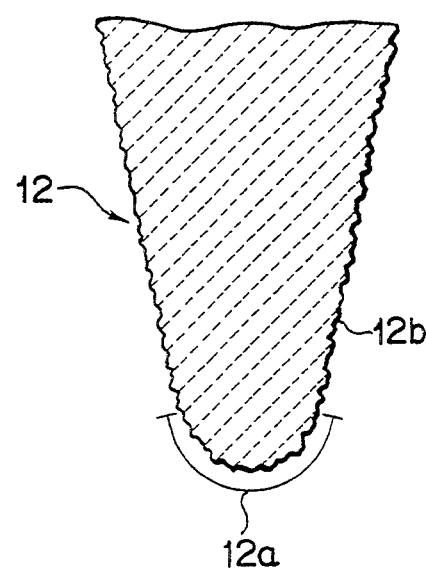
FIG. 3 is an enlarged sectional view of the tip end portion of the probe of FIG. 1.
Figure 4:
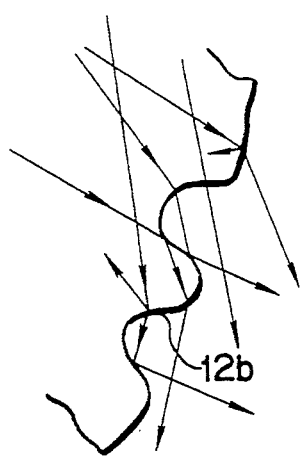
FIG. 4 is a further enlarged sectional view of the surface portion of the probe of FIG. 1 showing the diffusion modes of the laser beam.

As best shown in FIGS. 3 and 4, the outer surface of the laser diffusing portion 12 is frosted or roughened to form an uneven, pseudo-random contour defined by generally convex protuberances and concave recesses. The surface irregularity or recess depth is between about 1 to 100 $\mu$m, preferably 10 to 60 $\mu$m. The frosting or roughening process is preferably carried out by use of a computer controlled grinding wheel. More specifically, the probe undergoing surface treatment is rotated and then brought into contact with a diamond grindstone. The grindstone traces the unroughened contour of the probe, commencing from the tip 12a of the probe, as far rearward along the conical surface as desired to define the diffusing portion 12 thereof. The computer controls, in a conventional manner, the position and speed of travel of the grindstone. In one preferred arrangement, a grindstone having particles of between 10 and 20 $\mu$m is utilized while the grindstone is moved along the probe between 3 and 6 mm/second. A roughened surface condition defined by approximately 10 $\mu$m recesses results.

It will be appreciated that the depth of the recesses may be varied by utilizing grindstones of appropriate diamond particle size. However, as the recess depth is lowered, particularly below the preferred range set forth above, increasing percentage of the laser energy will be internally reflected within the probe tip thereby resulting in a correspondingly lesser amount laser energy being refracted and diffused radially outwardly. Such a tip will not exhibit the desired broad and uniform radiation patterns. As the other extreme, increasing the surface roughness beyond the preferred limits results in the tissue becoming entangled in the concaved recesses when the probe is inserted into the tissue thereby inhibiting withdrawal of the probe.

Operation of the present probe can best be understood with reference to FIG. 4 where the laser beam coupled into the probe from the optic guide is shown to be internally impinging the roughened surface 12b of the probe tip. This laser energy is illustrated by rays 31 and 33. It will be noted that these rays do not arrive in parallel relationship, but rather, impinge from differing angles representative of the fact that each has travelled its own independent path including, in the general case, having undergone unpredictable internal reflections from the irregular surface thereabove.

Depending upon both the incident angle and the specific point of intersection of the incoming ray with the roughened surface 12b, the ray is either reflected internally, to again strike the surface 12b, or refracted externally to radiate from the probe. In the general case, the laser energy may, in fact, split; that is, some energy is reflected while the rest is refracted and radiated. FIG. 4 depicts several representative ray tracks illustrating complete reflection, complete refraction, and a combination of both modes.

It is significant that the laser energy radiated from the probe is not directed in any particular direction, but rather, radiates in virtually all directions. In this manner, laser energy is emitted radially from the probe and, unlike conventional laser probes, can penetrate tissue lying radially adjacent the probe tip. It is, in short, this pseudo-random scattering or diffusing of laser energy which accounts for the significant radiation along the probe tip as depicted at 21 in FIG. 6.

Figure 7:
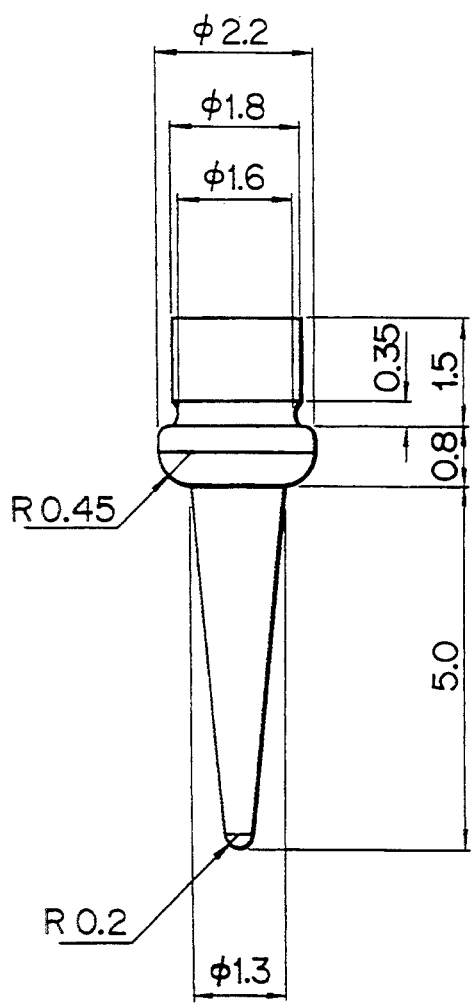
FIG. 7 is an elevation view of one example of the probe of the present invention showing the dimensions thereof.
Figure 5:
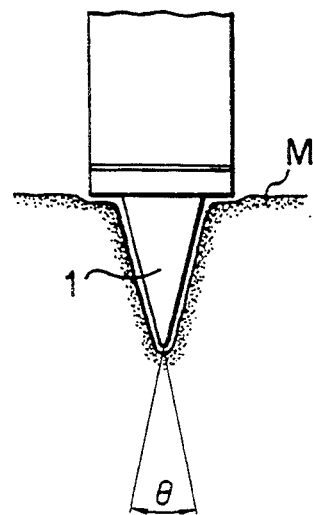
FIG. 5 is an elevation view of a non-diffusing probe inserted into the tissue and irradiating the tissue immediately below the probe tip.

FIG. 7 shows typical dimensions of one embodiment of the present probe. It will be appreciated that these dimensions are merely illustrative and the probe may advantageously be dimensioned according to specific treatment requirements. For example, the length of the laser diffusing portion 12 of the probe 10 may be suitably selected according to the insertion depth of the probe into the tissue M and it may in general be within a range of about 1.0 to 7.0 mm. Although the tip end of the laser diffusing portion 12 is not always required to be in semispherical shape, a pointed end would possibly be broken and therefore the tip end of the laser diffusing portion is preferably rounded.

In the embodiment described above, substantially the entire conically tapered portion function to diffuse laser energy therefrom. Alternatively, any limited or fractional portion of this conical section, including the tip end 12a, may serve as a laser diffusing portion by correspondingly restricting the degree of surface roughness. The flange 16 as described before functions as an abutment or stop for positioning of the probe 10 in the tissue M when the probe 10 is injected into the tissue M until the forward end face of the projected flange 16 abuts against the tissue M. However, the flange 16 may of course be omitted as the case may be.

Figure 9:
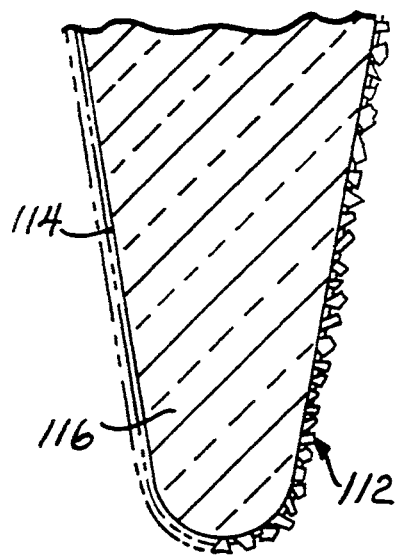
FIG. 9 is a sectional view of the tip end portion of another embodiment of the probe of the present invention having a particulate diffusing layer comprising diamond particles; and, FIG. 10 is an enlarged sectional view of the surface portion of the probe of FIG. 9 showing the diffusion modes of the laser beam.
Figure 10:
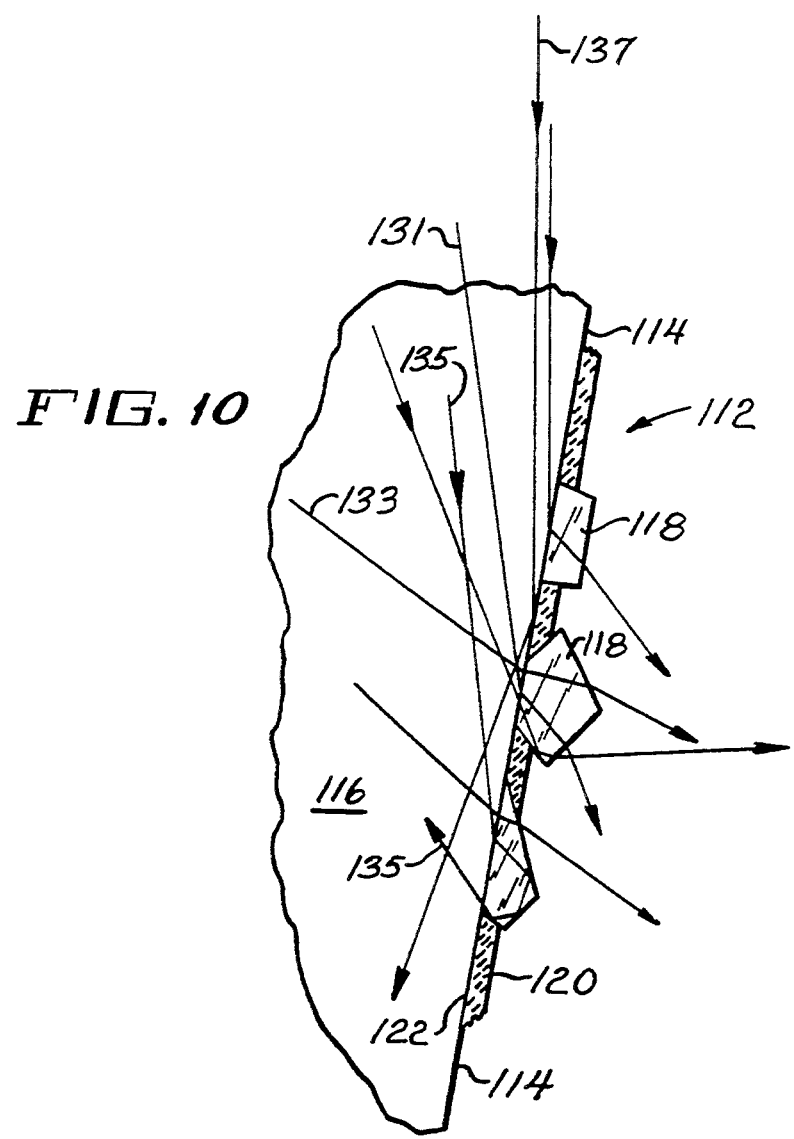

FIGS. 9 and 10 illustrate a further embodiment of the present invention in which a particulate diffusing layer 112 is applied and bound to the smooth outer surface 114 of a conical probe tip 116, preferably sapphire. The particulate layer comprises a plurality of irregularly shaped particles 118 of a laser transmissive material bonded to the probe tip 116 by a ceramic bonding agent 120.

Preferably particles 118 of the diffusing layer 112 will be diamond due to the high refractive index thereof. Thus, where the diffusing particles are diamond and the probe tip is sapphire substantial laser energy, which would otherwise be reflected internally at the sapphire/air interface, is coupled from the probe tip 116, that is, refracted into a diamond particle of the diffusing layer 112, in turn, being radiated randomly therefrom as shown in FIG. 10.

It will be understood that diffusing particles 118 having a refractive index less than that of diamond, but preferably still relatively high (e.g. sapphire, quartz, etc.), may be used by reason that the laser energy impinging the probe/diffusing layer interface 122 will, with greater probability, be refracted into the diffusing layer. This is due to the fact that the lowered ratio of refractive indices of the two adjoining materials will favor refraction at incident angles where (absent a diffusing portion) internal reflection would normally occur.

It is preferred that, in general, the size of the diffusing particles 118 be at least about equal to one half the wavelength of the laser energy produced by the laser employed; in the case of the Nd:YAG laser, wavelength is about 1060 nm.

In a further of its aspects, the invention is a method of making a probe having a laser diffusing particulate layer 112 bonded to a probe tip 116. Although, as mentioned above, both the probe tip and the particulate layer may be made of any of several laser transmissive materials, which may have the same or different refractive indices, the preferred embodiment of such a probe comprises a sapphire probe tip and a diamond particle diffusing layer. Hereinafter, reference may therefore be made to the sapphire probe tip and the diamond particle diffusing layer; and it should be understood that other combinations of materials could be employed for the probe tip 116 and the diffusing particles 118 of the diffusing layer 112.

In the probe of the invention, comprising a diamond particle layer 112, the diamond particles 118 are held in laser transmissive communication with the probe tip 116 by a ceramic material 120. Powdered ceramic materials which when heated to a high temperature bind sapphire and diamond, for example, are well known in the art. The ceramic powder (i.e. the ceramic bonding agent 120 before being exposed to thermal cycling) and diffusing particles 118 are admixed in a ratio appropriate to result, after the ceramic 120 is baked onto the probe, in a diffusing layer 112, wherein the diffusing particles are tightly adherent to the probe tip and in laser-transmitting communication therewith.

To make a probe of the invention having a refractive particulate diffusing layer, a slurry is made by mixing suitably sized refractive particles, generally in the range of about 0.5 $\mu$m to about 50 $\mu$m, with a ceramic powder which will bind the diffusing particles to the probe tip, in the presence of a suitable ceramic binder, such as a cellulose ester based binder, which binder will be substantially completely volatilized during the heating step causing, in turn, the particulate containing ceramic to bind to the probe tip. The slurry is applied and baked onto the probe tip at high temperature as described in detail immediately below.

A preferred method for making a sapphire probe of the invention having a diamond particle diffusing layer is performed as follows: A slurry is made by mixing 0.04 g of natural diamond powder (average size 1–3 $\mu$m), 0.04 g ceramic powder (83.5% Silicone Oxide; 1% Potassium; 15.5% Lead Oxide), 0.17 g ceramic binder (Astro-Met Associates, Inc., Woodlawn, Ohio; Product No. 3.0%–228-97) and 0.025 g distilled $H_2O$. Although this slurry composition is preferred, varying the ratio of diamond particles to ceramic powder from a ratio of about 3:1 to about 1:3 is within the scope of the invention. The slurry is applied by clasping the sapphire probe with a device adapted to hold the probe, with the tip 116 exposed in such a way that the probe and clasping device may be rotated very slowly about a horizontal axis, while the slurry is applied to the probe tip, for example, using a drill revolving at a very low speed. The slurry is worked onto the slowly-revolving probe tip with a very fine tipped paint brush or other instrument, until a thin, even coat is achieved, as determined with the aid of a low power objective (e.g., ~10×magnification). The slurry is applied to a sapphire probe tip 116 along that portion of the outer surface 114 of the probe where laser emission is desired, and allowed to air dry.

The diamond particles 118 are caused to adhere to the probe during a thermal cycle, wherein the air-dried, slurry-coated probe is heated in an oven to a temperature sufficient to melt the ceramic powder, which allows said ceramic 120 to flow into the interstices between the diamond particles. Upon cooling, the ceramic material 120 hardens and causes the diamond particles 118 to adhere to the surface of the sapphire probe tip 116. During the cycle, the oven is heated at a stepped-rate of 2.7° F./min from 70° to 1475° F. (8.7 hrs) and held at 1475° F. for 20 min, before it is cooled back to 70° by steps of 2.7° F./min. Thus, a full thermal cycle takes approximately 17¾ hours.

In an alternative method for making the particle-coated probes of the invention, the probe is coated with a thin layer of a low viscosity cyanoacrylate ester (e.g., Formula No. 18014; Loctite Corp., Newington, Conn. 06111) or similar adhesive. A low viscosity adhesive allows a very thin layer of diamond particles to be coated onto the probe tip 116. 0.04 g of natural diamond powder (average size 1–3 μm) and 0.04 g ceramic powder (83.5% Silicone Oxide; 1% Potassium; 15.5% Lead Oxide) are admixed and applied to the probe as it is slowly rotated horizontally about its axis. The admixed powders can be applied for example by sprinkling or sifting or by blowing them onto the probe tip 116 with air pressure. Because the cyanoacrylate dries quickly, the application of the mixture will be time-sensitive. The so-treated probes are heated using the same thermal cycling protocol as described above. The cyanoacrylate ester substantially vaporizes in the heating process, leaving the diamond particles 118 bound by the ceramic material 120 to the surface of the probe tip.

Operation of the probe comprising a diamond or other highly refractive particulate diffusing layer 112 can best be understood with reference to FIG. 10 where the laser beam coupled into the probe from the optic guide is shown to be internally impinging the particulate diffusing layer 112. This laser energy is illustrated by rays 131–137. As previously noted these rays do not necessarily arrive in parallel relationship, but, rather, impinge from differing angles, having undergone a combination of internal reflection at the probe/diffusion layer interface 122, and, in certain instances, internal reflection(s) within individual diamond particles 118 of the diffusion layer which latter reflections may direct the laser energy back into the probe tip 116, as best visualized in FIG. 10, by ray 135.

Depending on the ratio of the refractive indices between the diffusing particles and the probe tip, the location where the laser energy impinges the interface 122 between the probe tip and the particulate layer, laser energy will either be internally reflected or refracted into the diffusing particles. Because of the high refractive index of the diffusing particles 118, a significant portion of laser energy, which would otherwise be internally reflected by a smoothly contoured laser probe tip, is refracted into a diffusing particle 118. And depending on the shape of the individual diffusing particle 118, the incident energy may be directly refracted and radiated from the particle along the side of the probe or it may be first reflected within said particle one or more times. Where the laser energy impinges at the probe tip/ceramic interface, the ray may be internally reflected depending upon the refractive index of said ceramic 120. This is depicted by ray 137 in FIG. 10. It is this random diffusion, enabled by the high refractive index of the particulate diffusing material, and the irregular shapes of these particles which result in the broad radial diffusion of laser energy attained.

Figure 8:
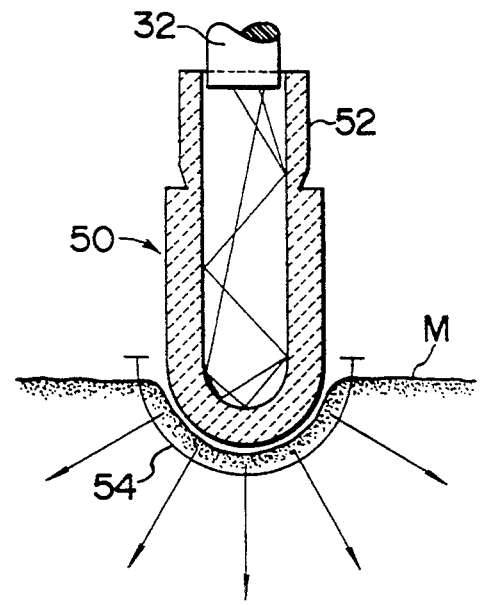
FIG. 8 is an elevation view, shown in section, of another embodiment of the probe according to the present invention.

FIG. 8 illustrates yet another embodiment of the present invention. Probe 50 has a substantially U-shaped cross-section and comprises a receiving portion 52 on the periphery of the base portion thereof for connection with the female connector 18 as described above. The outer and inner face of the probe have a semispherical shape and a frosted or roughened face is formed on the inner semispherical face and a part of a cylindrical portion adjacent to said inner semispherical face to provide a laser diffusing portion 54. Another portion of the inner face and the outer face remain smooth. The optical fiber 32 is disposed in the receiving portion of the probe 50. Most of the laser beam radiated from the tip end face of the optical fiber 32 enters the laser diffusing portion 54 where it is diffused and thereafter radiated from the outer surface of the tip end portion. This probe, which is brought into contact with the tissue rather than being inserted therein, is utilized for local hyperthermia, coagulation or photochemical therapy.

We claim:

1. A medical laser delivery system for conveying laser energy from a source of laser energy to a tissue undergoing laser treatment; the delivery system comprising laser transmissive material having a laser energy input region for receiving laser energy from a laser source and a laser energy radiation surface for emitting laser energy from the delivery system; laser energy diffusing means, said diffusing means comprising laser transmissive particles of irregular shape and means for affixing the particles to the laser energy radiation surface, the particles affixed so that laser energy emitted from the radiation surface may be coupled into the particles and irregularly refracted and reflected thereby causing a wide laser energy radiation profile, the affixing means and the particles forming a tissue contact surface for directly contacting the tissue undergoing treatment, a substantial number of the particles partially extending from the affixing means.

2. The medical laser delivery system of claim 1 in which the laser transmissive material includes an optical fiber having respective first proximal and second distal ends, said first proximal end defining the laser energy input region, and a probe member operatively connected to the second distal end of the optical fiber, the radiation surface defined on the probe member.

3. The medical laser delivery system of claim 1 wherein the particles which partially extend from the affixing means form a rough contact surface.

4. The medical laser delivery system of claim 3 wherein the rough contact surface defines an outer plane which consists solely of particles.

5. The medical laser delivery system of claim 3 wherein the rough contact surface has an irregular and uneven surface defined by recesses of between about 1 micron and about 100 microns.

6. The medical laser delivery system of claim 2, wherein the probe member is of a conical shape.

7. The medical laser delivery system of claim 1 wherein the particles are of a type and shape so as to cause at least some of the laser energy emitted from the laser energy radiation surface to be reflected by the particles back into the laser transmissive material and subsequently emitted from the laser energy radiation surface at a location different than the initially emitted location.

8. The medical laser delivery system of claim 1 wherein the particles are at least partially embedded in the affixing means.

9. The medical laser delivery system of claim 1 wherein the laser energy radiation surface is smooth.

10. The medical laser delivery system of claim 1 wherein the particles are diamond and the laser transmissive material is sapphire.

11. The medical laser delivery system of claim 1 wherein the particle affixing means comprises a ceramic bonding agent.

12. The medical laser delivery system of claim 1 wherein the particles have a cross-sectional dimension generally of at least one half the wavelength of the laser energy employed by the delivery system.

13. A medical laser probe for conveying laser energy from the output end of an optical laser waveguide to a tissue undergoing laser treatment; the probe comprising laser transmissive material having a laser energy input region for receiving laser energy from an optical waveguide and a laser energy radiation surface for emitting laser energy therefrom; laser energy diffusing means, said diffusing means comprising laser transmissive particles of irregular shape and means for affixing the particles to the laser energy radiation surface, the particles affixed so that laser energy emitted from the radiation surface may be coupled into the particles and irregularly refracted and reflected thereby causing a wide laser energy radiation profile, the affixing means and the particles forming a tissue contact surface for directly contacting the tissue undergoing treatment, a substantial number of the particles partially extending from the affixing means.

14. The medical probe of claim 13 in which the particle affixing means comprises a ceramic bonding agent.

15. The medical probe of claim 13 in which the particles have a cross-sectional dimension generally of at least one half the wavelength of the laser energy employed by the probe.

16. The medical probe of claim 13 wherein the particles which partially extend from the affixing means form a rough contact surface.

17. The medical probe of claim 16 wherein the rough contact surface defines an outer plane which consists solely of particles.

18. The medical probe of claim 16 wherein the rough contact surface has an irregular and uneven surface defined by recesses of between about 1 micron and about 100 microns.

19. The medical probe of claim 13 in which the laser transmissive material includes an optical fiber having respective first proximal and second distal ends, said first proximal end defining the laser energy input region, and a probe member operatively connected to the second distal end of the optical fiber, the radiation surface defined on the probe member.

20. The medical probe of claim 13 wherein the particles are of a type and shape so as to cause at least some of the laser energy emitted from the laser energy radiation surface to be reflected by the particles back into the laser transmissive material and subsequently emitted from the laser energy radiation surface at a location different than the initially emitted location.

21. The medical probe of claim 13 wherein the particles are at least partially embedded in the affixing means.

22. The medical probe of claim 13 wherein the laser energy radiation surface is smooth.

23. The medical probe of claim 13 wherein the particles are diamond and the laser transmissive material is sapphire.

24. A medical laser delivery system for conveying laser energy from a source of laser energy to a tissue undergoing laser treatment, the delivery system comprising (a) laser transmissive material having a laser energy input region for receiving laser energy from a laser source and a laser energy radiation surface for emitting laser energy from the delivery system;

(b) a layer comprising laser transmissive particles for diffusing laser energy passing therethrough; and (c) means for affixing the particles to the laser energy radiation surface whereby laser energy emitted from the radiation surface may be coupled into the particles and irregularly refracted and reflected thereby causing a wide laser energy radiation profile, the affixing means and the particles forming a tissue contact surface for directly contacting the tissue undergoing treatment, a substantial number of the particles partially extending from the affixing means.

25. The medical laser delivery system of claim 24 wherein the particles which partially extend from the affixing means form a rough contact surface.

26. The medical laser delivery system of claim 25 wherein the rough contact surface defines an outer plane which consists solely of particles.

27. The medical laser delivery system of claim 25 wherein the rough contact surface has an irregular and uneven surface defined by recesses of between about 1 micron and about 100 microns.

28. The medical laser delivery system of claim 24 in which the laser transmissive material includes (i) an optical fiber having respective first proximal and second distal ends, said first proximal end defining the laser energy input region, and (ii) a probe member operatively connected to the second distal end of the optical fiber, the radiation surface defined on the probe member.

29. The medical laser delivery system of claim 28, wherein the probe member is of a conical shape.

30. The medical probe of claim 29 wherein the particle affixing means comprises a ceramic bonding agent.

31. The medical probe of claim 29 wherein the particles have a cross-sectional dimension generally of at least one half the wavelength of the laser energy employed by the probe.

32. The medical laser delivery system of claim 24 wherein the particles are of a type and shape so as to cause at least some of the laser energy emitted from the laser energy radiation surface to be reflected by the particles back into the laser transmissive material and subsequently emitted from the laser energy radiation surface at a location different that the initially emitted location.

33. The medical laser delivery system of claim 24 wherein the particles are at least partially embedded in the affixing means.

34. The medical laser delivery system of claim 24 wherein the laser energy radiation surface is smooth.

35. The medical laser delivery system of claim 24 wherein the particles are diamond and the laser transmissive material is sapphire.

36. The medical laser delivery system of claim 24 wherein the particle affixing means comprises a ceramic bonding agent.

37. The medical laser delivery system of claim 24 wherein the particles have a cross-sectional dimension generally of at least one half the wavelength of the laser energy employed by the delivery system.

38. A medical laser probe for conveying laser energy from the output end of an optical laser waveguide to a tissue undergoing laser treatment, the probe comprising
(a) laser transmissive material having a laser energy input region for receiving laser energy from an optical waveguide and a laser energy radiation surface for emitting laser energy therefrom;
(b) a layer comprising laser transmissive particles for diffusing laser energy passing therethrough; and
(c) means for affixing the particles to the laser energy radiation surface whereby laser energy emitted from the radiation surface may be coupled into the particles and irregularly refracted and reflected thereby causing a wide laser energy radiation profile, the affixing means and the particles forming a tissue contact surface for directly contacting the tissue undergoing treatment, a substantial number of the particles partially extending from the affixing means.

39. The medical probe of claim 38 wherein the particles which partially extend from the affixing means form a rough contact surface.

40. The medical probe of claim 39 wherein the rough contact surface defines an outer plane which consists solely of particles.

41. The medical probe of claim 39 wherein the rough contact surface has an irregular and uneven surface defined by recesses of between about 1 micron and about 100 microns.

42. The medical probe of claim 38 in which the laser transmissive material includes
(i) an optical fiber having respective first proximal and second distal ends, said first proximal end defining the laser energy input region, and
(ii) a probe member operatively connected to the second distal end of the optical fiber, the radiation surface defined on the probe member.

43. The medical probe of claim 42 wherein the probe member is of a conical shape.

44. The medical probe of claim 42 wherein the probe member is of a conical shape.

45. The medical probe of claim 38 wherein the particles are of a type and shape so as to cause at least some of the laser energy emitted from the laser energy radiation surface to be reflected by the particles back into the laser transmissive material and subsequently emitted from the laser energy radiation surface at a location different than the initially emitted location.

46. The medical probe of claim 38 wherein the particles are at least partially embedded in the affixing means.

47. The medical probe of claim 38 wherein the laser energy radiation surface is smooth.

48. The medical probe of claim 38 wherein the particles are diamond and the laser transmissive material is sapphire.

49. A medical laser delivery system for conveying laser energy from a source of laser energy to a tissue undergoing laser treatment, the delivery system comprising
(a) laser transmissive material having a laser energy input region for receiving laser energy from a laser source and a laser energy radiation surface for emitting laser energy from the delivery system; and
(b) laser energy diffusing means comprising
(i) laser transmissive particles for diffusing laser energy passing therethrough, and
(ii) means for affixing the particles to the laser energy radiation surface, the particles affixed so that laser energy emitted from the radiation surface may be coupled into the particles and irregularly refracted and reflected thereby causing a wide laser energy radiation profile, a substantial number of the particles partially extending from the affixing means.

50. The medical laser delivery system of claim 49 in which the laser transmissive material includes an optical fiber having respective first proximal and second distal ends, said first proximal end defining the laser energy input region, and a probe member operatively connected to the second distal end of the optical fiber, the radiation surface defined on the probe member.

51. The medical laser delivery system of claim 50, wherein the probe member is of a conical shape.

52. The medical laser delivery system of claim 49 wherein the particles are of a type and shape so as to cause at least some of the laser energy emitted from the laser energy radiation surface to be reflected by the particles back into the laser transmissive material and subsequently emitted from the laser energy radiation surface at a location different than the initially emitted location.

53. The medical laser delivery system of claim 49 wherein the particles are at least partially embedded in the affixing means.

54. The medical laser delivery system of claim 49 wherein the laser energy radiation surface is smooth.

55. The medical laser delivery system of claim 49 wherein the particles are diamond and the laser transmissive material is sapphire.

56. The medical laser delivery system of claim 49 wherein the particle affixing means comprises a ceramic bonding agent.

57. The medical laser delivery system of claim 49 wherein the particles have a cross-sectional dimension generally of at least one half the wavelength of the laser energy employed by the delivery system.

* * * * *